US009759646B2

United States Patent
Oikonomou

(10) Patent No.: US 9,759,646 B2
(45) Date of Patent: Sep. 12, 2017

(54) SCALE MONITORING AND INHIBITOR QUANTIFICATION TECHNIQUE IN MULTIPHASE METERS

(71) Applicant: Roxar Flow Measurement AS, Stavanger (NO)

(72) Inventor: Dimitrios Oikonomou, Bergen (NO)

(73) Assignee: Roxar Flow Measurement AS, Stavanger (NO)

( * ) Notice: Subject to any disclaimer, the term of this patent is extended or adjusted under 35 U.S.C. 154(b) by 0 days.

(21) Appl. No.: 15/025,384

(22) PCT Filed: Oct. 16, 2014

(86) PCT No.: PCT/EP2014/072226
§ 371 (c)(1),
(2) Date: Mar. 28, 2016

(87) PCT Pub. No.: WO2015/055767
PCT Pub. Date: Apr. 23, 2015

(65) Prior Publication Data
US 2016/0216196 A1   Jul. 28, 2016

(30) Foreign Application Priority Data
Oct. 16, 2013   (NO) .................................. 20131375

(51) Int. Cl.
*G01R 27/08*   (2006.01)
*G01N 17/00*   (2006.01)
(Continued)

(52) U.S. Cl.
CPC ............. *G01N 17/008* (2013.01); *G01F 1/56* (2013.01); *G01F 1/64* (2013.01); *G01F 1/712* (2013.01);
(Continued)

(58) Field of Classification Search
CPC ...... G01N 17/00; G01N 17/006; G01N 17/02; G01N 17/04; G01N 27/02; G01N 27/04;
(Continued)

(56) References Cited

U.S. PATENT DOCUMENTS 4,774,680 A   9/1988   Agar
6,182,504 B1   2/2001   Gaisford
(Continued)

FOREIGN PATENT DOCUMENTS

GB   2246866 A   2/1992
WO   WO-0165212 A1   9/2001
(Continued)

OTHER PUBLICATIONS

Michalitsch, Richard, "International Search Report," prepared for PCT/EP2014/072226, as mailed Dec. 16, 2014, four pages.
(Continued)

*Primary Examiner* — Jermele M Hollington
*Assistant Examiner* — Raul Rios Russo
(74) *Attorney, Agent, or Firm* — Winstead PC

(57) ABSTRACT

The present invention relates to a system for detecting deposits or chemical inhibitor close to or on the surface of electrodes or pins facing a fluid flow where any combination of the components oil, water, gas and a chemical inhibitor fluid could be present, and where the electrodes or pins are coupled to measuring means for monitoring the electrical characteristics of the flow, the electrical characteristics including the complex impedance or complex permittivity. The system comprises detecting means transmitting a signal indicating presence of deposit or chemical inhibitor if the real part of the complex impedance, in case of hydrocarbon continuous flow, or the imaginary part of the complex
(Continued)

impedance, in case of water continuous flow deviates from predetermined limits related to the electrical characteristics of the said flow.

18 Claims, 7 Drawing Sheets

(51) Int. Cl.
| | | |
|---|---|---|
| G01F 1/712 | (2006.01) | |
| G01F 1/74 | (2006.01) | |
| G01N 27/02 | (2006.01) | |
| G01N 33/18 | (2006.01) | |
| G01F 25/00 | (2006.01) | |
| G01F 1/56 | (2006.01) | |
| G01F 1/64 | (2006.01) | |

(52) U.S. Cl.
CPC ............ *G01F 1/74* (2013.01); *G01F 25/0007* (2013.01); *G01N 27/026* (2013.01); *G01N 33/1833* (2013.01)

(58) Field of Classification Search
CPC .... G01L 1/10; G01L 1/20; G01L 1/22; G01R 27/00
USPC ......... 324/71.2, 76.11–76.83, 459, 600, 635, 324/639, 644, 649, 662, 671, 691, 693, 324/700, 716
See application file for complete search history.

(56) References Cited

U.S. PATENT DOCUMENTS

| | | | |
|---|---|---|---|
| 2003/0072549 A1* | 4/2003 | Facer ................... | C12N 13/00 385/129 |
| 2008/0283418 A1* | 11/2008 | Jovancicevic ......... | G01N 17/02 205/775.5 |
| 2010/0295565 A1* | 11/2010 | Drack .................. | G01F 23/243 324/693 |
| 2013/0154847 A1 | 6/2013 | Potyrailo et al. | |
| 2013/0162258 A1 | 6/2013 | Patin et al. | |

FOREIGN PATENT DOCUMENTS

| | | |
|---|---|---|
| WO | WO-2005057142 A1 | 6/2005 |
| WO | WO-2007018434 A1 | 2/2007 |
| WO | WO-2008085065 A1 | 7/2008 |
| WO | WO-2012007718 A2 | 1/2012 |

OTHER PUBLICATIONS

Bruggeman, D.A.G., "Berechnung verschiedener physikalischer Konstanten von heterogenen Substanzen"; Annalen der Physik 24, 5 Folge, Band 24; 1935; pp. 636-664.

Tjomsland, Tore, et al.; "Comparison of Infrared and Impedance Spectra of Petroleum Fractions"; Fuel, vol. 75, No. 3; Feb. 1996; pp. 322-332.

* cited by examiner

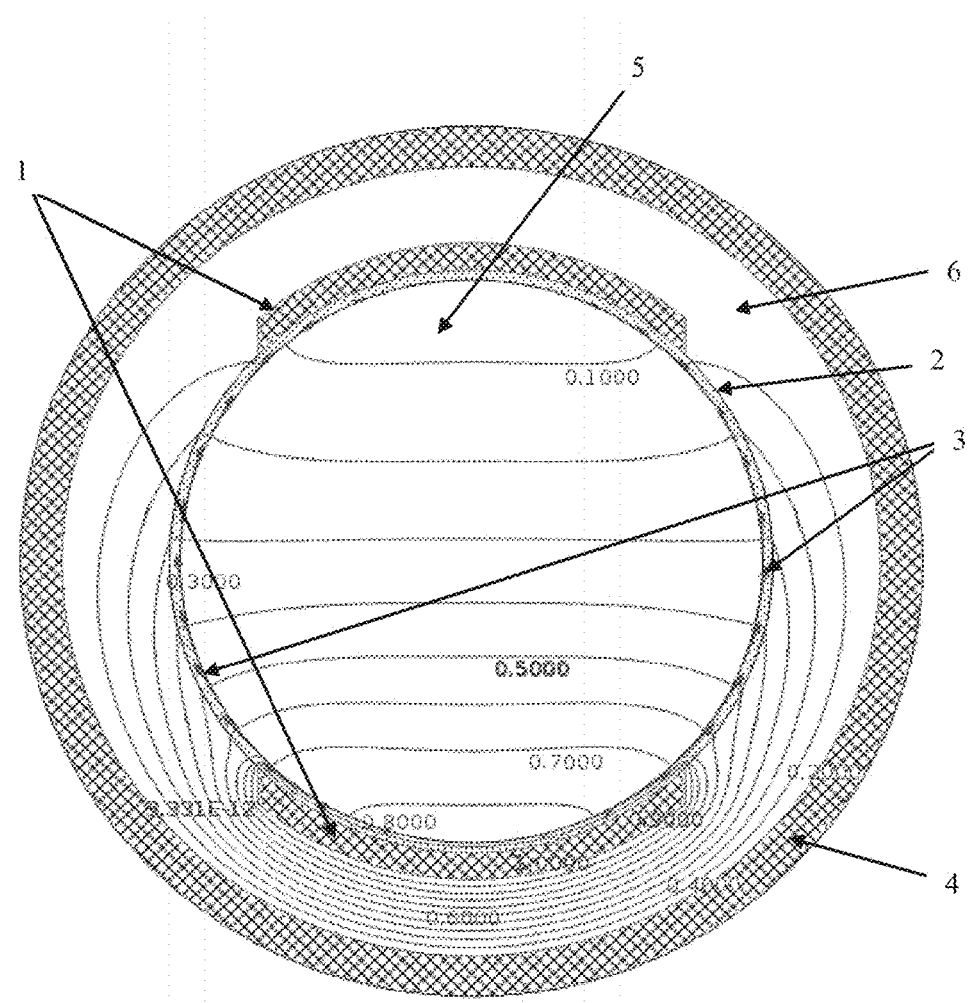
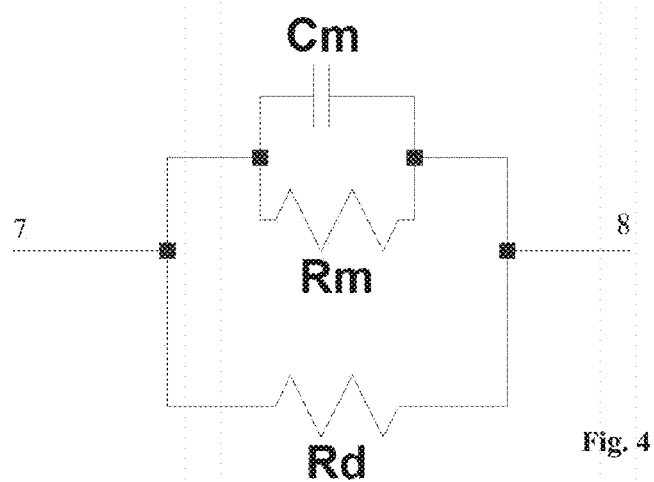
Fig. 3
Fig. 4

SCALE MONITORING AND INHIBITOR QUANTIFICATION TECHNIQUE IN MULTIPHASE METERS

The present invention relates to a system and method for early detection of deposit formation on pipe walls in process flows.

In performing measurements in multiphase flows such as water, oil and/or gas flows, it is a well-known problem that deposits may form on the measuring means having contact with the flow and thus affecting the quality of the measurements. The deposits may be removed in different ways or washed out by the flow. The necessity and time between cleaning may vary depending on the conditions and content in the flow. This invention will detect the onset of deposits before they affect the flow measurement sensors and provides a means for early handling of deposits. In the following, as deposits, we also consider chemicals injected in the flow to remove the deposits that may stick to the pipe, the sensor walls and electrodes. Such chemical injections, also called inhibitors, aim to prevent or remove deposits and clean the pipes and/or the sensor.

The content of a multi-phase flow may be estimated using electrodes measuring the impedance of the flow, i.e. by finding the permittivity and conductivity of the flow. Several such solutions are known, e.g. as discussed in WO2007/018434, WO2008/085065, WO2005/057142 and U.S. Pat. No. 6,182,504. In all these publications, the measurements are performed by electrodes in contact with the fluid flow, and the quality of the measurements may be diminished by scaling or deposits accumulating on the electrodes. WO01/65212A1 discusses the problem with the deposition of materials and other environmental effects on the measurement performance, and proposes the use of calibration liquid to compensate for the errors, but does not provide a method to detect the onset of the deposits especially because the publication does not comprise a technique to distinguish deposits from other error sources. GB2246866A recites the use of impedance measurements, however, does not go farther than to mention that depending upon whether the flow behaves as water-continuous or oil-continuous, the impedance measurements are dominated by the real or the imaginary part, with the other one being negligible. There is, hence, no technique provided in said totality of prior art towards the use for detection of deposits.

The aim of the present invention is to provide a means for real-time detection of deposits on the meter body, so that cleaning and, if needed, calibration or adjustments in the measurements may be performed at an early stage before any effect on the quality of the measurements. This is achieved by the method and system specified in the independent claims. Furthermore, the present invention allows for the development of standalone sensors capable of early deposit detection in pipes.

The present invention is based on the realization that certain electrical characteristics measured in the flow do not correspond to the nature of the flow. For example, an oil continuous flow does not have a significant conductivity, while a water continuous flow displays variable conductivity depending on the salinity of the flow, but no significant capacitance. As these parameters may be calculated by monitoring the complex impedance of the pipe contents measured by the sensor, it is possible to detect the formation of deposits by analyzing the trend of the sensor output values with respect to the expected values or a model thereof.

A rather general approach would be to measure the complex impedance of the flow with electrodes. Complex impedance, in electrical impedance measurement context, has a real part (conductance) and an imaginary part (reactance), the reactance dominantly being capacitance in the case of a flow measurement sensor. As a general characteristic, the flow composition passing between the sensor electrodes typically varies over time, so the real and the imaginary part measured by the sensor vary proportionally to the fluid composition. To sense the presence of the deposits or other chemicals such as inhibitor, the analysis of irregular behavior in the sensor output values is proposed in the present invention.

In flow measurement context, the real and the imaginary parts of the complex impedance measured are related to the conductivity and dielectric constant/permittivity of the process respectively. Measurements are performed either at low frequencies, usually below 10 MHz, wherein complex impedance of the process is directly measured, or alternatively, at high frequencies, usually higher than 10 MHz, wherein complex permittivity is measured. In high frequency measurements, usually performed using microwave probes, the complex permittivity is used to describe the electrical characteristics of the process. Microwave probes working as transmitters are receivers are used to measure the parameters such as phase and amplitude, which are then related to the real and imaginary parts of the complex permittivity of the process.

The relative complex permittivity ($\in^*_r$) is a dimensionless quantity, which compares the complex permittivity of a material ($\in^*$) to the permittivity of the free space $\in_0$ ($\in_0 = 8.854 \cdot 10^{-12}$ F/m). It describes the interaction of a material with the electric field and consists of a real part $\in'_r$, which represents the energy storage capability, and an imaginary part $\in''_r$, which represents the losses. The real part of the relative permittivity ($\in'_r$) is a measure of how much energy from an external electric field will be stored by the material. It is frequently referred to as the "dielectric constant" and is related to the flow capacitance. For most solids and liquids $\in'_r > 1$ and for most gases $\in'_r \cong 1$. The imaginary part of the relative permittivity (Er) is called the "loss factor" and is related to flow conductivity.

The present invention will be described in detail below with reference to the accompanying drawings, illustrating the invention by way of examples.

FIG. 3 illustrates the electrode constellation according to a first embodiment of the invention.

FIG. 4 illustrates the modification to the simplified equivalent electrical circuit seen by the sensor in the case of a conductive layer deposit in oil continuous flow regimes.

FIG. 5a, 5b illustrate an embodiment of the signal processing system according to the present invention using time period measurements to accomplish the complex impedance measurement.

Maxwell (1904), Bruggeman (1935), Wagner (1973), Sillars (1937) (see complete reference below) and many others have developed formulae for the estimation of the effective complex permittivity of homogeneous mixtures of two different phases. Effective complex permittivity is the permittivity of a virtual material which when replaces a mixture of two or more materials displays identical electromagnetic behavior.

For simplicity the case where one of the components (salt water) is of high conductivity compared to the other one (oil and/or gas) will be discussed here and the purpose is to estimate the normal flow effective complex permittivity in oil continuous and water continuous flow states. Normal complex permittivity is defined in this document as the expected values of the real and imaginary part of the effective complex permittivity of a three phase flow that an impedance or microwave sensor will measure in the absence of a deposit.

Case of Oil Continuous Flow (Water in Oil W/O)

Figure 1:
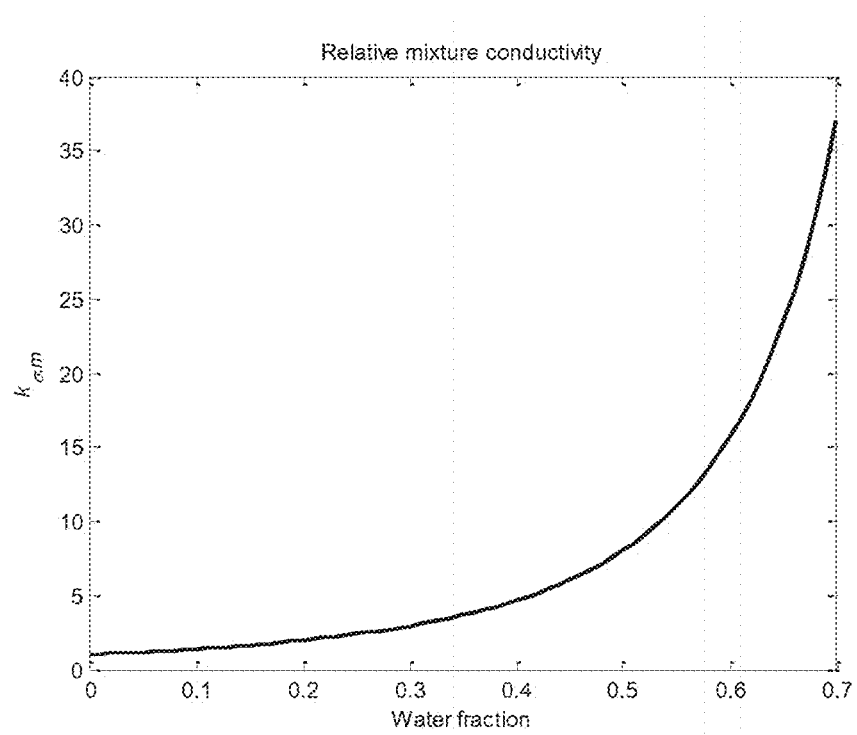
FIG. 1 illustrates the mixture conductivity of a multiphase flow as a function of the water fraction.

The mixture effective conductivity $\sigma_m$ in W/O, according to (Hanai, 1963) (see complete reference below) is related to the oil conductivity $\sigma_o$ by the formula $$k_{\sigma,m} = \frac{\sigma_m}{\sigma_o} = \frac{1}{(1-\beta)^3}$$

where $\beta$ is the water fraction ratio. FIG. 1 shows the increase of the $k_{\sigma,m}$, of the mixture conductivity, compared to the oil conductivity.

Figure 2:
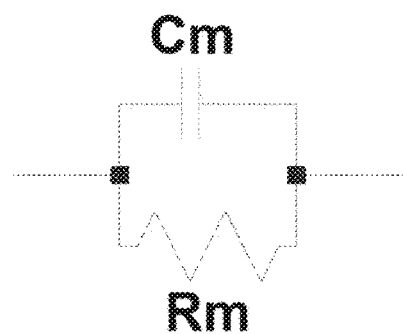
FIG. 2 illustrates a simplified equivalent electrical circuit of the flow mixture as seen by the sensor.

The equivalent electrical circuit of the mixture that the sensor measures is illustrated in FIG. 2 where, $C_m$ and $R_m$ are the effective medium capacitance and resistance respectively.

Although the Hanai formula is just one of the ways to estimate the effective mixture conductivity, it can calculate with acceptable accuracy the range of expected values and in close agreement with all published work (Bruggeman etc.). In case of oil continuous flow regimes, and considering that the flow state turns to water continuous when the water fraction is higher than 50-70%, it has been realized by analysis performed by the inventor of the present invention that the expected maximum flow effective conductivity, or normal flow conductivity, will not be higher than 40 times the pure oil conductivity. The inventor has devised a method, based on transient analysis of the sensor response, to measure the flow impedance rather than conductivity. Equivalently, the statement defining said maximum flow effective conductivity limit can be modified as; in oil continuous flow regimes the real part of the flow impedance will not be lower than ¹⁄₄₀ times the real part of the impedance of pure oil medium flowing through the exact same meter with no deposits or chemical inhibitor.

In oil continuous flow regime, when deposits of conductive nature are either due to free electrons or due to ionic conductivity layer at the walls of the sensor, the measured effective conductivity can be much higher than the expected one. If the increase of the measured effective conductivity is 60 times or more than the pure oil conductivity then the sensor can reliably provide a signal that a layer of conductive nature has formed on the meter walls, as supported by the analysis performed by the inventor. As discussed before, said analysis indicate that the water dispersed in the oil can induce a maximum increase of the conductivity of the mixture by a factor of approximately 40.

FIG. 3 shows the sensor casing 4 consisting of two electrodes 1 embedded in an insulating material 6 where a conductive deposit 2 (illustrated by dotted area) has developed, and a conductive current 3 (illustrated by arrows) is running through the deposit layer increasing the effective conductivity of the oil continuous flow 5. The contour lines in the drawing illustrate electric potential (V) and the arrows current density. Said conductive current is a kind of leakage that is an undesired parameter for proper functioning of the meter.

The conductive or leakage current due to the effect of deposit can be monitored even if a single electrode is used, for example in the case of coaxial microwave probes, where the leakage current will flow from the central pin of the probe through the conductive deposit layer to the meter body. The same holds true for sensors comprising more than 2 electrodes as soon as a conductive leakage path due to the deposit layer develops between the exciting electrode or pin and another electrode or pin or the meter body, allowing the flow of an undesired conductive current.

FIG. 3, discussed above, shows a vertical cross section to the flow of an impedance sensor comprising two impedance measuring electrodes 1 in contact with the flow traversing through the conduit enclosed by the inner surface of the meter body. The flow is in oil continuous state and therefore no significant conductive current is running through the flow. A leakage current, shown with arrows, is running between the electrodes through the conductive layer deposited on the inner surface of the meter body. The electric displacement field isolines are also shown in the figure.

The article by Tore Tjomsland et. al. (see complete reference below) discusses issues regarding the imaginary part of permittivity for various crude oils versus frequency.

It is important to notice here that early detection of the deposit layer can be achieved using the idea described in this invention without measuring the mixture capacitance. An a priori knowledge of the type of the flow (in this case oil continuous) together with a conductivity measurement that is 60 times higher than the conductivity of pure oil are enough to conclude that there is a conductive deposit layer, as proposed in the present invention.

Additionally, considering that typical oil conductivity is in the range of nanoS/m to picoS/m, while the conductivity in a water continuous flow is in the S/m region, the current invention will pick up the existence of a deposit layer/chemical injection when the mixed conductivity falls in the microS/m to nanoS/m region, well below the measurement region interpreted by a flow meter as water continuous i.e. the S/m to milliS/m conductivity range.

An example is the case, in oil continuous flow state, where the static conductivity is used to monitor the existence of a deposit layer by measuring the conductance between a conducting pin of 2 mm radius by 5 mm height with 1 cm insulation between the pin and the metal body of the A conductive layer made of material with conductivity of 1 S/m will increase the mixed conductivity by a factor of 60 compared to the oil conductivity when the layer thickness falls in the range of nanometers, a thickness probably not visible to an experienced engineer. Additionally, in most cases such a deposit burden does not affect the performance of a flow measurement device. In this sense, a flow measurement device not utilizing the current invention cannot be used for monitoring the onset of deposit layers. Since the injection of deposit inhibitor chemicals typically has a similar effect on the measurements as in the case of a deposit layer, the prior art will fail in detecting traces or low concentration of inhibitor injections as well, unlike the present invention.

The electric network shown in FIG. 4 presents a simplified equivalent circuit for the case of conductive deposit layer in oil continuous flow regimes connected between one exiting electrode/pin 7 and another electrode/pin or meter body 8. The components $C_m$ and $R_m$ represent the parameters of interest for flow measurement and are the same as introduced in FIG. 2.

In this network, of FIG. 4, $C_m$ and $R_m$ are used to describe the complex impedance of the flow while $R_d$ is the resistance of the deposit layer, which is inversely proportional to the conductivity of the deposit layer. If $R_d$ is considerably less than the minimum $R_m$ that a W/O mixture can display then $$\frac{1}{R_m \| R_d} \approx \frac{1}{R_d}$$

and as a result the sensor measured mixture conductivity will be dominated by the conductivity of the layer and the sensor can provide a signal for the existence of the conductive deposit layer.

It is also worth commenting that as there is no change in the importance of measured capacitance $C_m$ of the network, and it still being a measurement parameter of interest, the sensor should therefore be designed carefully in order to, a) be able to measure the complex impedance of the flow, b) cover the extended dynamic range for the real part of complex impedance mandated by the $R_d$ measurement, c) be able to measure the flow capacitance $C_m$ with sufficient accuracy in presence of the conductive leakage current, and as a result, d) allow accurate flow fraction calculations, without degradation of performance when the deposit volume fraction is small enough compared to the volume of the sensor.

Figure 5B:
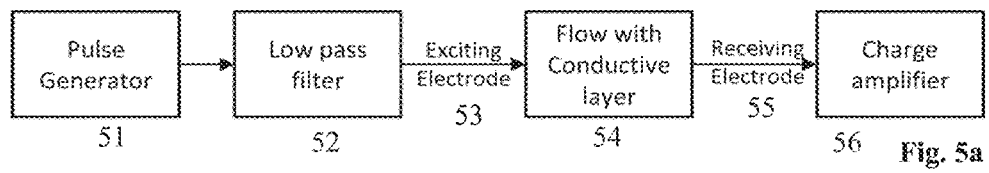
Figure 5B:
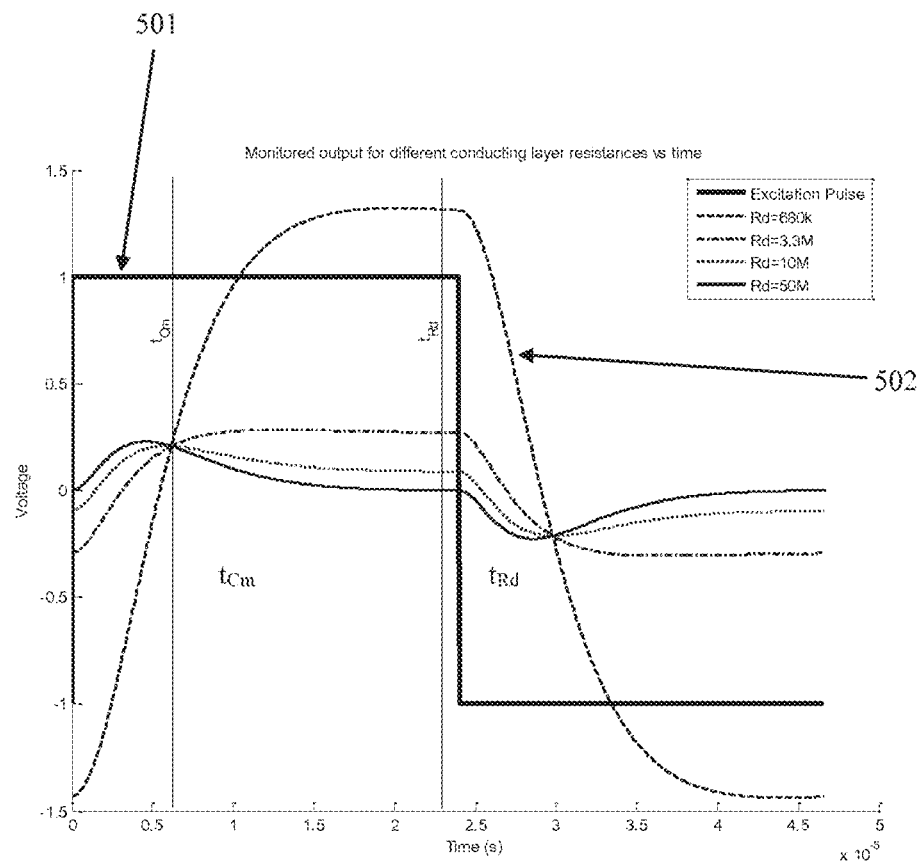

An embodiment of the technique described by the present invention, in targeting the measurement of both the flow capacitance and the layer conductance, may be achieved using the transient analysis of the system response when the sensor is excited by a low pass filtered rectangular pulse 502. As illustrated in FIGS. 5a and 5b, in such implementation a rectangular pulse 501 is generated by a pulse generator 51 while the low pass filter 52 defines the frequency of interest for the measurement to be implemented. The signal 502 excites the flow 54 through an electrode 53 and a second electrode 55 is used to monitor the current flowing through a charge amplifier 56, realized for example as, a low impedance input miller integrator with a finite DC feedback. FIG. 5a presents an example of the signal handling system, the complete signal processing system will comprise the output of the charge amplifier 56 connected to a suitable signal conversion means, such as an ADC, followed by digital signal processor that stores and analyses the measurements and the trend thereof. Said signal processor may also comprise storage means, such as digital memory, for storing mathematical models for comparison and analysis, with the models being adapted according to the environmental factors, for example, to improve the measurement accuracy.

Through a careful selection of components and electrical analysis on the exciting and receiving sub-circuits, sampling times $t_{Cm}$ and $t_{Rd}$ can be defined that will enable the simultaneously accurate measurement of the flow capacitance and layer resistance respectively as it is shown in FIG. 5b. The time $t_{Cm}$ is here defined as the time from excitation to of the pulse, until the equal voltage point, i.e, the time where the output voltage remains undisturbed by changes in the parallel resistance. Here, the capacitance of the flow (for this case 0.2 pF) is measured correctly at time $t_{Cm}$ regardless of the size of the layer resistance, which is measured at time $t_{Rd}$. The time $t_{Rd}$ is when the output voltage has reached a stable value, and certainly shorter than the half period of the excitation pulse. The selection of these two time steps may be performed by a person as part of an instrumentation electronics development procedure or similar. The pulse length should be sufficient to make sure that the frequencies selected by the low pass filter can excite the electrode. The mapping of output voltages to flow capacitance (output voltage at sampling time $t_{Cm}$) and layer resistance (output voltage at sampling time $t_{Rd}$) is achieved usually through calibration during the production of the electronics.

It is shown in the same FIG. 5b that the measurement is very fast and a single measurement of both, flow capacitance and layer resistance can be completed in half period of the excitation pulse. In the specific example, the frequency of the excitation pulse is 22 kHz and the low pass filter 3 dB frequency is at 100 kHz, enabling the continuous monitoring of the effective flow complex impedance with a time resolution better than 25 microseconds.

The selection of the pulse and the 3 dB low pass filter frequencies as well as the exciting and receiving sub-circuit components have to be designed as dictated by the knowledge of the meter and electrodes/pins sizes, the targeted values and the dynamic range of the capacitances and resistances to be dealt with while implementing the technique.

Case of Water Continuous Flow (Oil in Water O/W)

Figure 6:
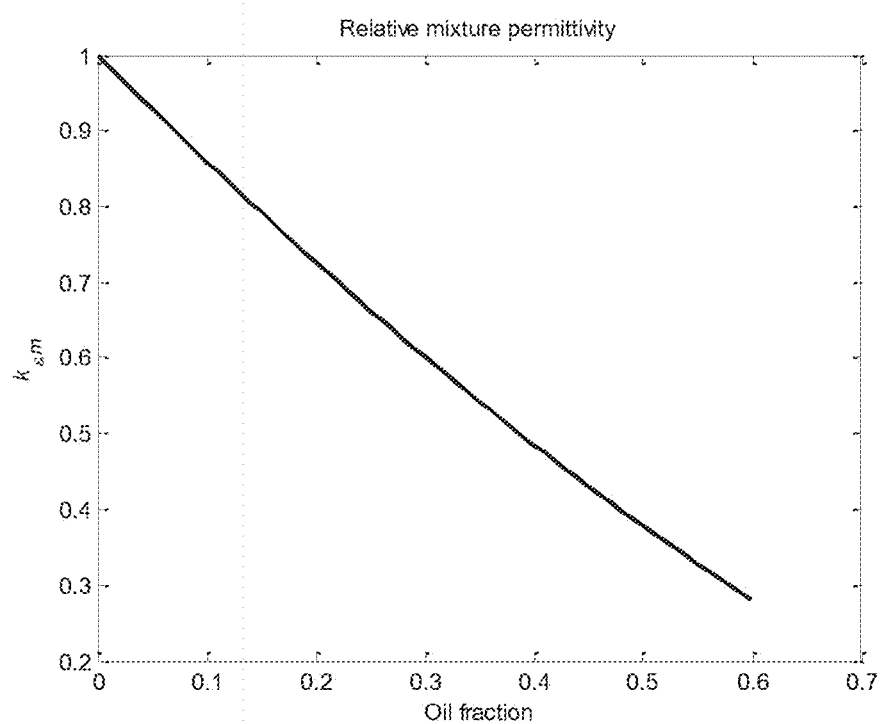
FIG. 6 illustrates the permittivity as a function of the oil fraction in a water continuous flow.

The real part of the mixture effective permittivity ($\in_m$) in O/W, according to (Hanai, 1963) is related to the oil ($\in_o$) and water permittivity ($\in_w$) by the formula $$\frac{2\varepsilon_m - 3\varepsilon_o}{2\varepsilon_w - 3\varepsilon_o} = (1 - \Phi)^{3/2}$$

where $\Phi$ is the oil fraction ratio and $\Phi = 1-\beta$, with $\beta$ the water fraction ratio. Assuming a water real part of permittivity as 81 and oil real part of permittivity as 2.2, values that are found in the literature and used in the document only for understanding the technique, the relative real part of permittivity of O/W mixture is changing by a factor $$k_{\varepsilon,m} = \frac{\varepsilon_m}{\varepsilon_w}$$

as shown in FIG. 6.

Hence, the real part of the effective medium permittivity decreases as the amount of oil increases and the flow remains in the water continuous phase.

Figure 7:
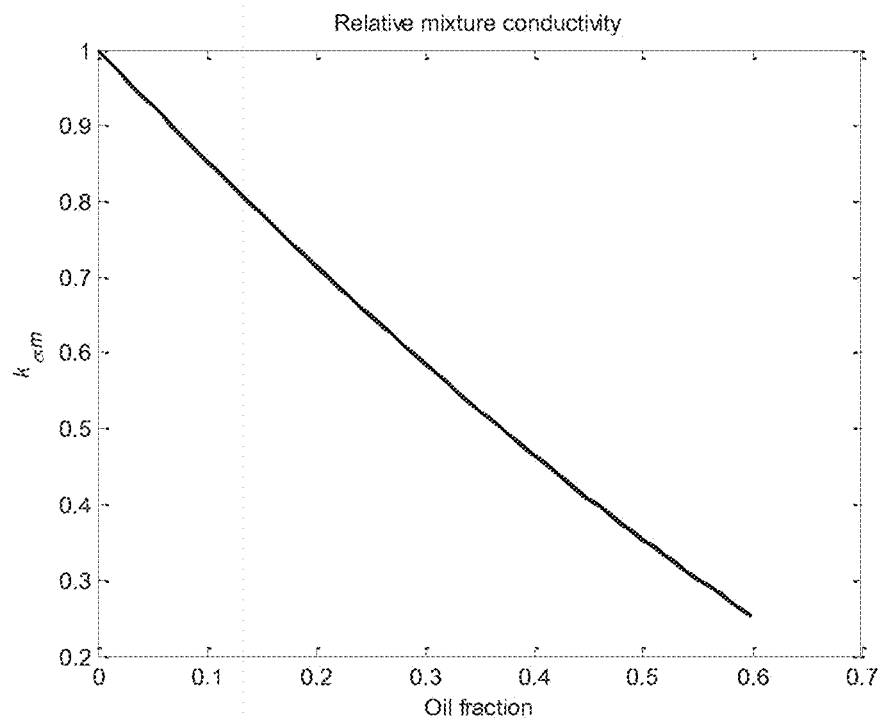
FIG. 7 illustrates the conductivity as a function of the oil fraction in a water continuous flow.

The imaginary part of the mixture effective permittivity in O/W, is related to the water fraction ratio by the formula $$k_{\sigma,m} = \frac{\sigma_m}{\sigma_w} = (1 - \Phi)^{3/2}$$

as illustrated in FIG. 7 where Φ is the oil fraction ratio. Hence the imaginary part of effective medium permittivity, related to mixture conductivity, decreases as the amount of oil increases and the flow remains in the water continuous phase.

Again referring to the equivalent electrical circuit of the mixture that the sensor measures as illustrated in FIG. 2, now the capacitance $C_m$ of the effective medium decreases and the resistance $R_m$ of the effective medium increases as oil fraction increases and the mixture remains in water continuous state, where $$R_m = \frac{L}{A} \cdot \frac{1}{\sigma_m}$$

with L the length, A the cross sectional area and $\sigma_m$ the conductivity of the resistor $R_m$.

In water continuous flow the presence of salt in water makes the water conductive and as a result when the sensor excites the flow, the current through $C_m$ will be bypassed by $R_m$. It can be shown that for 100% water fraction the current through $C_m$ is equal to the current through $R_m$ if the measurement is made at a frequency $f_c$ given by:

$$f_c = \frac{\sigma_w}{2\pi\varepsilon_0\varepsilon_w}$$

Where $\varepsilon_0$ is the permittivity of free space ($\varepsilon_0$=8.854·10⁻¹² F/m).

For $\sigma_w$=1 S/m and $\varepsilon_w$=81 the frequency that these currents are equal in amplitude is calculated in the range of 220 MHz.

Considering that the measurement in water continuous flow is made at frequencies significantly lower than $f_c$, the complex permittivity is dominated by the imaginary part, whereby changes in the flow capacitance (real part of effective medium permittivity) are negligible for the purposes of flow measurements. Monitoring of minor changes of the flow capacitance in water continuous flow state is complicated due to parasitic effects in the electronics of the sensor, and the double layer polarization effect on the surface between the electrodes and the flow. The optimum frequency for making impedance measurements lies in the region of 10 kHz to 20 MHz where the double layer polarization effect is avoided.

Figure 8:
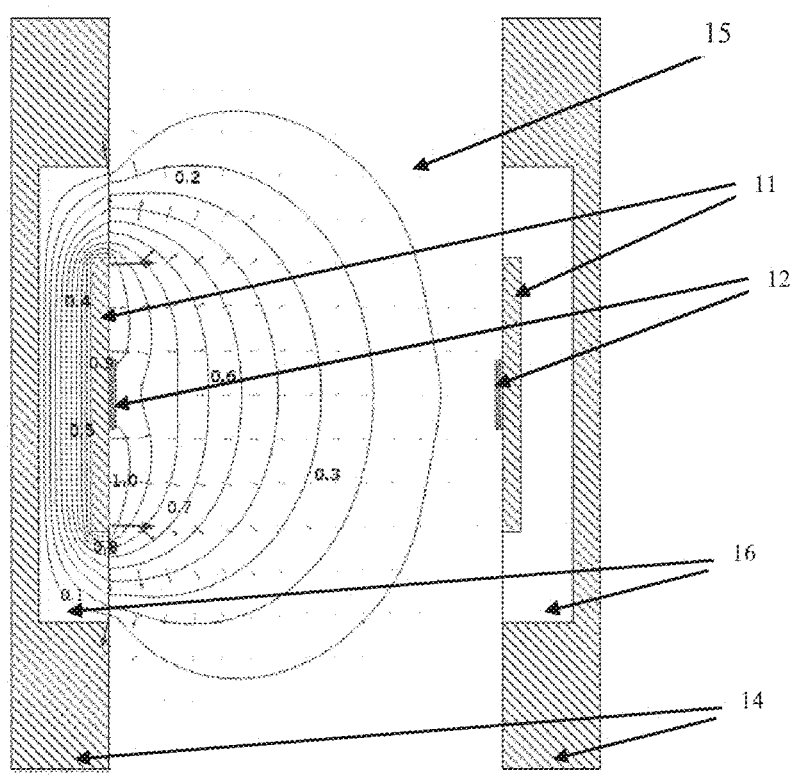
FIG. 8 illustrates the electrode configuration including a capacitive layer on part of the electrodes.

FIG. 8 illustrates an electrode configuration 11 including a capacitive layer 12 between electrode and flow 15. There is a voltage difference between the sides of the layer (one attached to the exciting electrode and the other to the flow). All parts of the exciting electrode are at equal potential value since it is a good conductor. The contour lines in the drawing illustrate electric potential (V) and the arrows current density (A/m²).

In the following example based on the configuration in FIG. 8 we see the vertical cross section of an impedance sensor consisting of two electrodes/pins 11, isolated from the meter body 14 by a non-conducting insulating material 16. The flow 15 is considered conductive and both electrodes 11 are partially covered by a capacitive layer 12 of area A and thickness d. The left electrode is considered the exciting electrode while the right one is the receiving electrode. It can be seen on the left capacitive layer that there is a voltage difference between the layer surface touching the electrode (Electrode voltage is 1 V) and the surface in contact with the flow (flow voltage is around 0.9 V). Assuming for simplicity that the voltages on both sides are constant and neglecting the electromagnetic effects near the top and bottom side of the capacitive layer, a plate capacitor is the electrical network equivalent to the electromagnetic phenomena of the layer. The capacitance of a plate capacitor can be defined as:

$$C = \varepsilon_l \varepsilon_0 \frac{A}{d}$$

where $\varepsilon_l$ is the real part of the relative complex permittivity of the material of the layer and $\varepsilon_0$ is the permittivity of free space. Considering an area surface A equal to 1 cm², thickness d of 0.5 mm and $\varepsilon_l$=2.5 the capacitance of the layer is in the range of 15 nF which is much higher than any possible capacitance measured with an impedance sensor in a water continuous, thus conductive flow. The detection of the layer is implemented by measuring the energy storage capability of the flow, including the capacitive layer. If there is no capacitive layer the conductive flow is not able to store a significant amount of charge, while the capacitive layer of the example shown will store charge equal to Q=C·ΔV=15 nF·0.1V=1.5 nCoulomb, where ΔV is the voltage difference between the capacitive layer sides. This excess of charge stored by the O/W flow, when there is a capacitive layer on the excitation electrode or pin, can by monitored by the sensor using well established techniques.

An implementation of this measurement is the transient analysis of the currents flowing through the sensor when a voltage pulse is applied to an exciting electrode similar to the implementation described for the W/O layer monitoring implementation.

As in the case of oil continuous flow, a capacitance or charge minimum threshold can be defined based on the measurement technique and the frequency/ies of the capacitance measurements. A measured capacitance or charge that exceeds this threshold signals the existence of a capacitive layer on the surface of the electrode or the pin. Again, the exact measurement of the effective conductivity of the process is not relevant to the detection of the capacitive layer. The system may measure the flow effective conductivity, to determine (using algorithms not relevant to the current invention) when the process state is in water continuous mode, or be designed to get the process state as an input.

Figure 9:
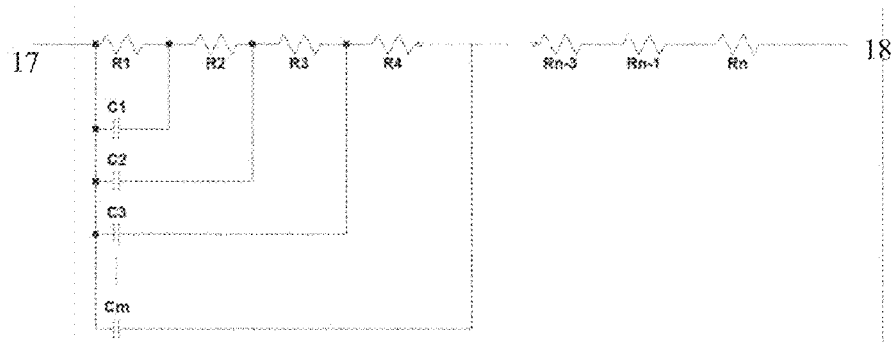
FIG. 9 illustrates a general electric network describing the effect of a capacitive layer on the electrodes/pins of the impedance sensor.

A general electric network describing the effect of a capacitive layer in the electrodes/pins of the impedance sensor is shown in FIG. 9, where resistors R1-Rn are used to describe the conductive nature of the flow and capacitors C1-Cm represent the distributed capacitance of the capacitive layer attached to the excitation probe. The network is connected between the exciting electrode/pin 17 and the receiving electrode/pin 18, or meter body.

Figure 10A:
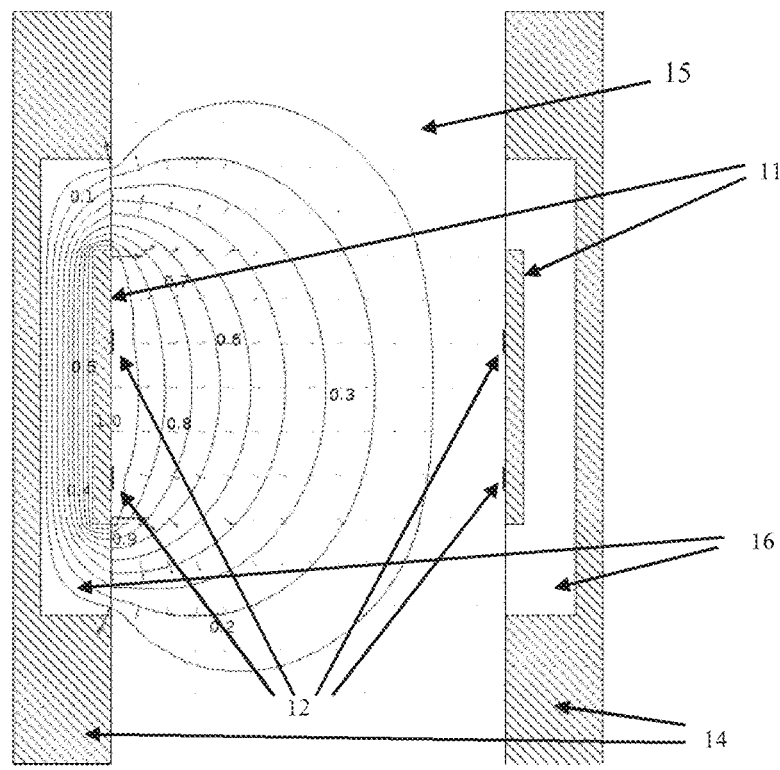
FIG. 10a, 10b illustrates the electrode configuration including two capacitive layers on the left and no capacitive layer on the right.
Figure 10B:
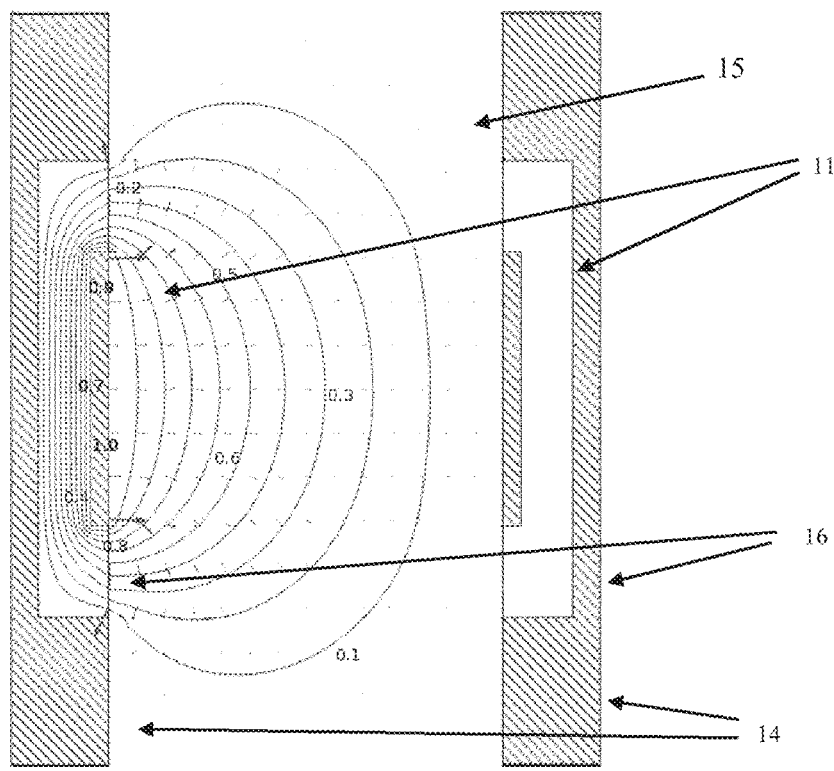

It is worth mentioning that the sensor will still be able to measure the flow resistance correctly provided that the capacitive layer is not covering a major area of the electrodes such that the conductive contact with the process is affected. Since the electrodes are conductive in nature, their entire surface is at the same potential, so as long as there is contact between the electrode and the flow, (exciting electrode 17 and R1) the steady state current of the network described above is not affected by the capacitances C1-Cm and a correct measurement of the flow conductivity can be made. The theory is still valid in practice since the capacitive layer will introduce only a near field effect close to the excitation electrode and have a negligible effect on the field at the receiving electrodes/pins. The next two figures, FIGS. 10a and 10b, illustrate this phenomenon. The electric potential distribution and the current density from a clean sensor and a sensor with two capacitive layers on the excitation and receiving probes are shown in a constellation comprising two capacitive layers in FIG. 10a and no layer in FIG. 10b. It is evident that at short distance from the exciting electrode, the field distributions in both cases are the same.

Figure 11:
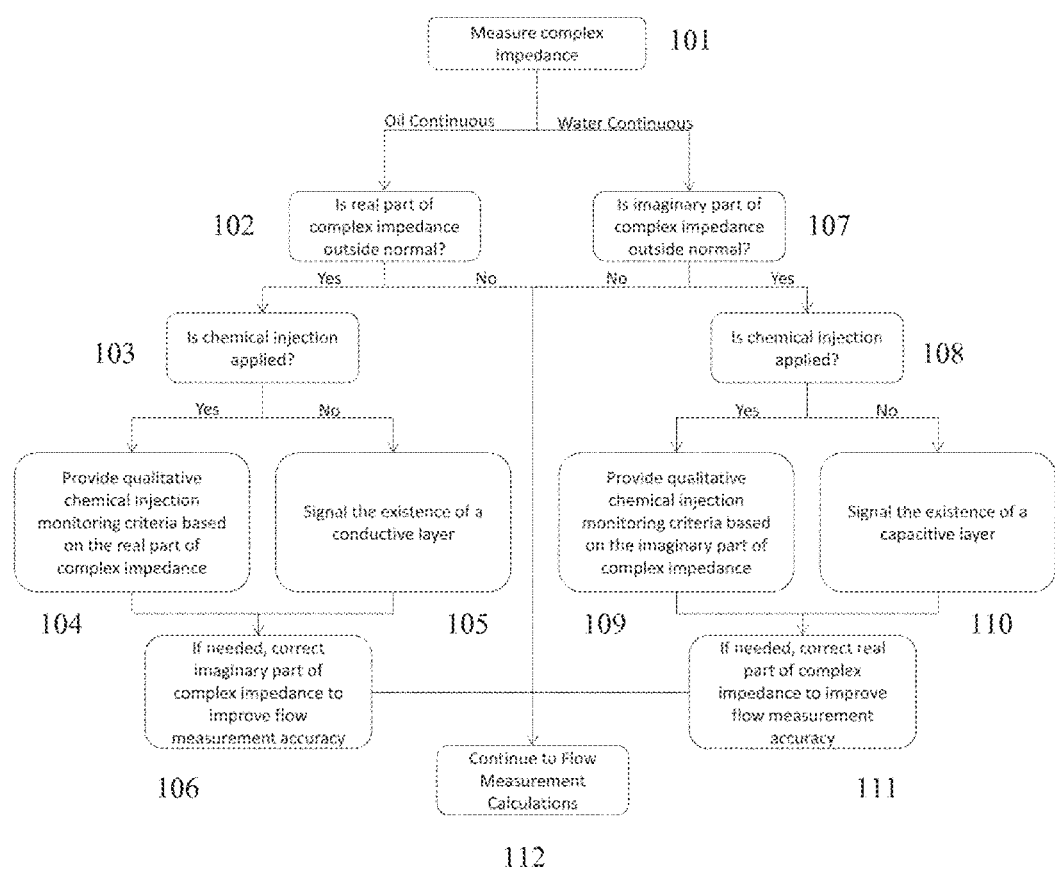
FIG. 11 illustrates an embodiment of the measurement sequence according to the present invention.

To sum up the measurement methodology, an example of the measurement sequence according to the present invention is illustrated in FIG. 11. According to this embodiment, a complex impedance is first measured 101. If this shows that the flow is oil or hydrocarbon continuous, it is determined whether the real part of the complex impedance is outside the normally expected values 102. The measurements can be evaluated and monitored over time, for example as a trend, to observe the progression of the deposits. The measurements can further be compared with a mathematical model of the sensor system stored in a storage medium, and said model adapted over time by the signal processing system or the operator to take into account the external influences such as pressure, temperature, and ageing, to improve the measurement accuracy over the lifetime of the system. The evaluation of trend of the measurements can further be used to decide the calibration of the system using techniques such as calibration liquids. If the measured values are within limits or according to the acceptable trend, the normal flow measurement calculations 112 are continued, but if they lie outside the normal range, the possibility of the presence of a chemical inhibitor is checked 103. Since the chemical inhibitor is usually injected on purpose, its presence can normally be anticipated, so the answer to the chemical injection question can usually be provided by the operator or other instruments controlling the chemical injection process.

If a chemical inhibitor has been applied, the chemical injection or inhibitor concentration in the flow is monitored qualitatively based on the real part of the complex impedance 104, but if not, a signal indicating the existence of a conductive layer on the electrodes is transmitted 105, e.g. to monitoring personnel or monitoring equipment.

In both cases, if needed, the imaginary part of the complex impedance may be corrected to improve the flow measurement accuracy 106, and the flow measurements may continue 112. Such a correction may involve correction for the measuring cross section or volume which might be decreased by the existence of the deposit in the pipe or even correction in the electrical measurement to take into account the electrical characteristics of the deposit.

Alternatively, if the first step 101 indicates that the flow is water continuous, the imaginary part of the complex impedance is evaluated 107. Similar to the measurement techniques explained for the real part 102, if within normal limits or trend, the flow measurement calculations are continued 112, if not, injection of a chemical inhibitor is considered 108.

If a chemical inhibitor has been applied, the chemical injection is monitored qualitatively based on the imaginary part of the complex impedance 109, if not, a signal indicating the existence of a capacitive layer on the electrodes is transmitted 110, e.g. to monitoring personnel or monitoring equipment.

In both cases, if needed, the real part of the complex impedance may be corrected to improve the flow measurement accuracy 111, and the flow measurements may continue 112. Such a correction may involve correction for the measuring cross section or volume which might be decreased by the existence of the deposit in the pipe or even correction in the electrical measurement to take account of the electrical characteristics of the deposit.

The sequence presented in FIG. 11 is repeated fully or partially at pre-determined time intervals to provide continuous monitoring of the deposits.

Thus to summarize, the invention relates to a method and system for real-time detection of deposits or chemical inhibitor on a surface close to electrodes facing a fluid flow, and where the fluid flow may include any combination of the components oil, water, gas and a chemical inhibitor fluid. The system comprises electrodes being coupled to measuring means for monitoring the electrical characteristics of the flow, the electrical characteristics including the complex impedance. The system enables early detection of said deposits before they affect measurements.

The system comprises detecting means transmitting a signal indicating the presence of deposit or chemical inhibitor if the monitored electrical characteristics deviation exceeds a predetermined limit from a prerecorded value, the prerecorded value being characteristic of the situation without deposit. The deviation is specifically defined in the real part of the complex impedance if the flow is a hydrocarbon continuous flow. If the flow is a water continuous flow the imaginary part of the electrical characteristics deviates from predetermined limits.

The system comprises detecting means transmitting a signal indicating if the real part of the complex impedance, in case of hydrocarbon continuous flow, or the imaginary part of the complex impedance, in case of water continuous flow deviates from predetermined limits related to the electrical characteristics of the said flow.

An identification of a deposit may then be registered and a signal may be transmitted indicating such a detection if the real part of the complex impedance or resistance is below a predetermined value, which will be the case in a hydrocarbon continues flow, or the imaginary part of the complex impedance or capacitance is above a predetermined value, which will be the case if the flow is a water continuous flow.

Thus the system and method according to the invention may include means, either based on the measured characteristics or otherwise, for determining if the flow is water or hydrocarbon continuous. The flow status as either oil- or water-continuous may be either an input to the system or be determined by methods known to the person, e.g. such as described in U.S. Pat. No. 4,774,680 or U.S. Pat. No. 6,182,504.

The predetermined limits indicating the detection of a deposit or injection may be a fixed value, but could also be a predetermined function, e.g a relative value. The measurements can be stored, evaluated and monitored over time, for example as a trend, to observe the accumulation of the deposits. The measurements can further be compared with a mathematical model of the sensor system and said model adapted over time to take into account the external influences such as pressure, temperature, and ageing, to improve the measurement accuracy over the lifetime of the system. The evaluation of trend of the measurements can further be used to decide the calibration of the system using techniques such as calibration liquids. The comparing means may include advanced multivariate or neural network methods comparing a number of different known or measured parameters related to the flow or simply by defining scale detection in a predetermined set of related parameters.

In this case the predetermined limits may be dynamically adjusted using means that provide composition and/or fractions and/or pressure and/or water salinity and/or temperature and/or rate and/or density measurements if the said measurements change the real part of the effective complex permittivity of the said multiphase flow in hydrocarbon continuous flow regimes or change the imaginary part of the effective complex permittivity of the said multiphase flow in water continuous flow regimes.

On the other hand a qualitative measurement of the deposit in the position of the sensor as well as evaluation of the pipe condition may be provided based on the real part of the complex impedance of the measured complex impedance if the flow is in hydrocarbon continuous state or based on the imaginary part of the complex impedance of the measured complex impedance if the flow is in water continuous state.

A measurement on the rate of growth of the deposit in the vicinity of the sensor may be provided based on periodic measurements or trend of the real part of the measured complex impedance if the flow is in hydrocarbon continuous state or based on the imaginary part of the measured complex impedance if the flow is in water continuous state.

In addition the effectiveness of a chemical inhibitor on removing a deposit may be measured by comparing the real part of the measured complex impedance if the flow is in hydrocarbon continuous state or based on the imaginary part of the measured complex impedance if the flow is in water continuous state before and after the inhibitor injection to the said flow. Also the quantity and/or rate and/or periods of a chemical inhibitor to be injected in a pipe for cleaning a deposit may be based on the effectiveness of the inhibitor against the said deposit monitored by the system.

The system and method may also include means for detecting or registering that a chemical inhibitor has been released into the said flow and take this information into account when analyzing the measured parameters. This may be obtained either by separate measurements of the injection flow line, or by receiving other indication (for example from the operator) that such inhibitor has been injected to the flow. The predetermined limits indicating either the existence of a deposit layer or the qualitative measurements of the inhibitor in the flow may then be adjusted based on the electrical and other characteristics of the inhibitor.

Thus the present invention relates to means for determining if the fluid flow is a water continuous or hydrocarbon continuous flow, the indication signal being transmitted by the comparing means if the fluid flow is a hydrocarbon continuous flow and the conductivity is above the predetermined limit. Alternatively or in addition the present invention relates to means for determining if the fluid flow is a water continuous or hydrocarbon continuous flow, the indication signal being transmitted if the fluid flow is a water continuous flow and the capacitance is above the predetermined limit. As a result of the detection of a deposit the system or method may include means for releasing a chemical inhibitor into the said flow to provide means for early handling of deposits.

ADDITIONAL REFERENCES

D. A. G. Bruggeman, Annalen Der Physik 24 (1935) 636-679.
J. C. Maxwell, A treatise on Electricity and Magnetism, Oxford University Press, Cambridge, UK, 1904.
K. W. Wagner K W (1914) Archiv für Elektrotechnik 1914, Volume 2, Issue 9, pp 371-387
R. W. Sillars, "The properties of a dielectric containing semiconducting particles of various shapes," Electrical Engineers, Journal of the Institution of, vol. 80, no. 484, pp. 378, 394, April 1937
T. Hanai, N. Koizumi and R. Gotoh, "The Dielectric Behavior of Emulsions", in P. Sherman, Ed., "Emulsion Rheology" p. 91-113, Pergamon Press, Oxford (1963).
Tore Tjomsland, Jannicke Hilland, et. al., "Comparison of infrared and impedance spectra of petroleum fractions", Fuel Vol. 75, No. 3, pp. 322-332, 1996.

The invention claimed is:

1. A system for real-time detection of a deposit or a chemical inhibitor that is close to or on a surface of electrodes or pins, the system comprising:
 a first sensor coupled to the electrodes or pins, wherein the first sensor is configured to:
  determine the electrical characteristics of a fluid flow, the electrical characteristics including real and imaginary parts of a complex impedance or a complex permittivity;
  simultaneously monitor the real and imaginary parts of the electrical characteristics through measurement of a transient response of the system; and
  measure the transient response of the system after exciting the electrodes or pins with a current or voltage waveform of a given profile;
 a signal processing system, the signal processing system configured to:
  compare transient response data with predetermined limits, models, or trends related to the electrical characteristics of the fluid flow that is stored on a storage medium;
  detect a deviation of the transient response data from the predetermined limits, models, or trends; and
  transmit a signal indicating a presence of the deposit or chemical inhibitor if the real part of the complex impedance, in case of hydrocarbon continuous flow, or the imaginary part of the complex impedance, in case of water continuous flow, deviates from the predetermined limits, models, or trends related to the electrical characteristics of the fluid flow.

2. The system according to claim 1, wherein the fluid flow is a hydrocarbon continuous flow and the signal processing system is configured to transmit a signal when the real part of the complex impedance or a resistance deviates from a predetermined limit or expected trend.

3. The system according to claim 2, wherein a minimum predetermined limit for the real part of the complex impedance is $1/40$ times a real part of an impedance of a pure oil medium flowing through the system without any deposits.

4. The system according to claim 2, wherein the minimum predetermined limit for the real part is of the complex impedance is $1/60$ times a real part of an impedance of a pure oil medium flowing through the system without any deposits.

5. The system according to claim 2, wherein the system is configured to transmit the signal when the deviation in the real part of the complex impedance is below a minimum predetermined limit.

6. The system according to claim 1, wherein the fluid flow is a water continuous flow and the signal processing system is configured to transmit a signal when the imaginary part of the complex impedance or a capacitance deviates from a predetermined limit or expected trend.

7. The system according to claim 2, wherein the system includes a second sensor to determine if the fluid flow is a hydrocarbon continuous flow or a water continuous flow.

8. The system according to claim 1, wherein the system is adapted to dynamically adjust the predetermined limits, models, or trends using a third sensor, the third sensor configured to provide measurements of environmental factors including, if the environmental factors change the real part of the complex permittivity of a multiphase flow in hydrocarbon continuous flow regimes, composition, fractions, pressure, water salinity, temperature, rate, and density, or to change the imaginary part of an effective complex permittivity of the multiphase flow in water continuous flow regimes.

9. The system according to claim 8, wherein the system is configured to define the predetermined limits, models, or trends by computations including known formulae to calculate effective medium impedances, multivariate regression models and analysis, and artificial neural networks.

10. The system according to claim 1, wherein the system is adapted to perform a qualitative measurement of the deposit in a vicinity of the electrodes or pins based on the real part of the complex impedance when the fluid flow is in a hydrocarbon continuous state or based on the imaginary part of the complex impedance when the flow is in a water continuous state.

11. The system according to claim 10, wherein the system is adapted to measure a rate of growth of the deposit based on continuous or periodic measurements and a historical trend of the real part of the complex impedance when the flow is in hydrocarbon continuous state, or based on the imaginary part of the complex impedance when the flow is in water continuous state.

12. The system according to claim 1, wherein the system is configured to adapt the predetermined limits, models, or trends based upon a known or anticipated amount of the chemical inhibitor.

13. The system according to claim 1, wherein the system is adapted to perform a qualitative measurement of the chemical inhibitor in a vicinity of the electrodes or pins based on the real part of the complex impedance when the fluid flow is in hydrocarbon continuous state or based on the imaginary part of the complex impedance when the fluid flow is in water continuous state.

14. The system according to claim 1, wherein the system is adapted to measure an effectiveness of the chemical inhibitor in removing the deposit by comparing the real part of the complex impedance when the flow is in a hydrocarbon continuous state or based on the imaginary part of the complex impedance when the flow is in a water continuous state before and after injection of the chemical inhibitor to the flow.

15. The system according to claim 10, wherein the system is configured to adapt at least one of a quantity, a rate, and a period of an injection of the chemical inhibitor in a pipe for cleaning the deposit based on at least one of an effectiveness of the chemical inhibitor against the deposit, the effectiveness monitored by the system and the qualitative measurement of the deposit in the vicinity of the electrodes or pins.

16. The system according to claim 1, wherein the system is adapted to determine a deviation in the real part of the complex impedance or a conductance by measuring a transient response at a chosen time $t_{Rd}$ after an excitation time $t_0$.

17. The system according to claim 1, wherein the system is adapted to determine a deviation in the imaginary part of the complex impedance or a capacitance by measuring a transient response at a chosen time $t_{Cm}$ after an excitation time $t_0$.

18. The system according to claim 1, wherein the system is adapted to predict and inform of a need of calibration to maintain a performance of the system based on a comparison of transient response data.

* * * * *